US010709633B2

(12) United States Patent
Kazerooni et al.

(10) Patent No.: US 10,709,633 B2
(45) Date of Patent: Jul. 14, 2020

(54) EXOSKELETON SUPPORT MECHANISM FOR A MEDICAL EXOSKELETON

(71) Applicant: The Regents of the University of California, Oakland, CA (US)

(72) Inventors: Homayoon Kazerooni, Berkeley, CA (US); Nicholas J. Errico, Oakland, CA (US); Katherine Marie Fearing, Orinda, CA (US); Wayne Yi-Wei Tung, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/197,129

(22) Filed: Nov. 20, 2018

(65) Prior Publication Data

US 2019/0151183 A1    May 23, 2019

Related U.S. Application Data

(60) Provisional application No. 62/588,824, filed on Nov. 20, 2017.

(51) Int. Cl.
*A61H 3/00* (2006.01)
*A61F 2/70* (2006.01)
(Continued)

(52) U.S. Cl.
CPC .............. *A61H 3/008* (2013.01); *A61F 2/70* (2013.01); *A61H 3/04* (2013.01); *B25J 9/0006* (2013.01);
(Continued)

(58) Field of Classification Search
CPC .. A61H 3/008; A61H 3/04; A61H 2201/1621; A61H 2201/0192;
(Continued)

(56) References Cited

U.S. PATENT DOCUMENTS 4,724,827 A * 2/1988 Schenck .............. A61H 1/0288
601/40
5,667,461 A * 9/1997 Hall ..................... A61H 1/0229
472/15
(Continued)

FOREIGN PATENT DOCUMENTS

CN    101810533 A    8/2010
GB    2231500 A    11/1990
(Continued)

OTHER PUBLICATIONS

"Int'l Application Serial No. PCT/US18/62097, Int'l Search Report and Written Opinion dated Mar. 11, 2019", 9 pgs.

*Primary Examiner* — Garrett K Atkinson
(74) *Attorney, Agent, or Firm* — Kwan & Olynick LLP

(57) ABSTRACT

A coupling device couples a walker to a torso orthosis which is coupled to a person. The coupling device includes an orthosis coupling member coupled to said torso orthosis, a walker coupling member coupled to said walker, and a mechanism coupled to the orthosis coupling member from its first end and to the walker coupling member from its second end. The mechanism constrains said orthosis coupling member to move along a free line. The torso orthosis is worn by the person and said coupling device is coupled to both said walker and said torso orthosis. The person may be walking along a moving direction not parallel with said free line. The mechanism forces said walker and torso orthosis to move along said moving direction and allows said torso orthosis to move freely along said free line when said moving direction is not parallel with said free line.

14 Claims, 19 Drawing Sheets

(51) Int. Cl.
*B25J 9/00* (2006.01)
*A61H 3/04* (2006.01)

(52) U.S. Cl.
CPC ... *A61F 2002/701* (2013.01); *A61F 2002/704* (2013.01); *A61H 2003/007* (2013.01); *A61H 2003/043* (2013.01); *A61H 2201/0192* (2013.01); *A61H 2201/165* (2013.01); *A61H 2201/1621* (2013.01)

(58) Field of Classification Search
CPC ........ A61H 2003/043; A61H 2003/007; A61H 2201/165; A61F 2/70; A61F 2002/701; A61F 2002/704; B25J 9/0006
See application file for complete search history.

(56) References Cited

U.S. PATENT DOCUMENTS

| | | | | |
|---|---|---|---|---|
| 6,123,649 | A * | 9/2000 | Lee | A63B 21/153 482/51 |
| 6,666,831 | B1 * | 12/2003 | Edgerton | A61H 1/0237 600/587 |
| 6,796,926 | B2 * | 9/2004 | Reinkensmeyer | A61B 5/1038 482/51 |
| 7,331,906 | B2 * | 2/2008 | He | A61H 1/0237 482/69 |
| 7,494,450 | B2 * | 2/2009 | Solomon | A61H 1/0229 482/51 |
| 7,887,471 | B2 * | 2/2011 | McSorley | A63B 21/0552 482/136 |
| 7,998,040 | B2 * | 8/2011 | Kram | A63B 21/4015 482/124 |
| 8,057,410 | B2 * | 11/2011 | Angold | A61H 3/00 601/35 |
| 8,608,479 | B2 * | 12/2013 | Liu | A61H 1/024 434/255 |
| 2003/0064869 | A1 * | 4/2003 | Reinkensmeyer | A61B 5/1038 482/100 |
| 2004/0087418 | A1 * | 5/2004 | Eldridge | A63B 21/157 482/54 |
| 2004/0204294 | A2 * | 10/2004 | Wilkinson | A63B 21/015 482/54 |
| 2005/0101448 | A1 * | 5/2005 | He | A61H 1/0237 482/54 |
| 2008/0300118 | A1 * | 12/2008 | Wehrell | A63B 21/04 482/129 |
| 2010/0204804 | A1 * | 8/2010 | Garrec | A61H 1/0277 623/24 |
| 2010/0270771 | A1 | 10/2010 | Kobayashi et al. | |
| 2011/0313331 | A1 * | 12/2011 | Dehez | A61H 1/0277 601/33 |
| 2013/0130866 | A1 * | 5/2013 | Wehrell | A61H 1/0229 482/5 |
| 2013/0225371 | A1 * | 8/2013 | Harrer | A63B 21/0552 482/8 |
| 2015/0297934 | A1 * | 10/2015 | Agrawal | A61H 1/0266 482/4 |
| 2017/0165145 | A1 | 6/2017 | Aryananda et al. | |

FOREIGN PATENT DOCUMENTS

GB 2541697 A 3/2017
WO 2019100072 5/2019

* cited by examiner

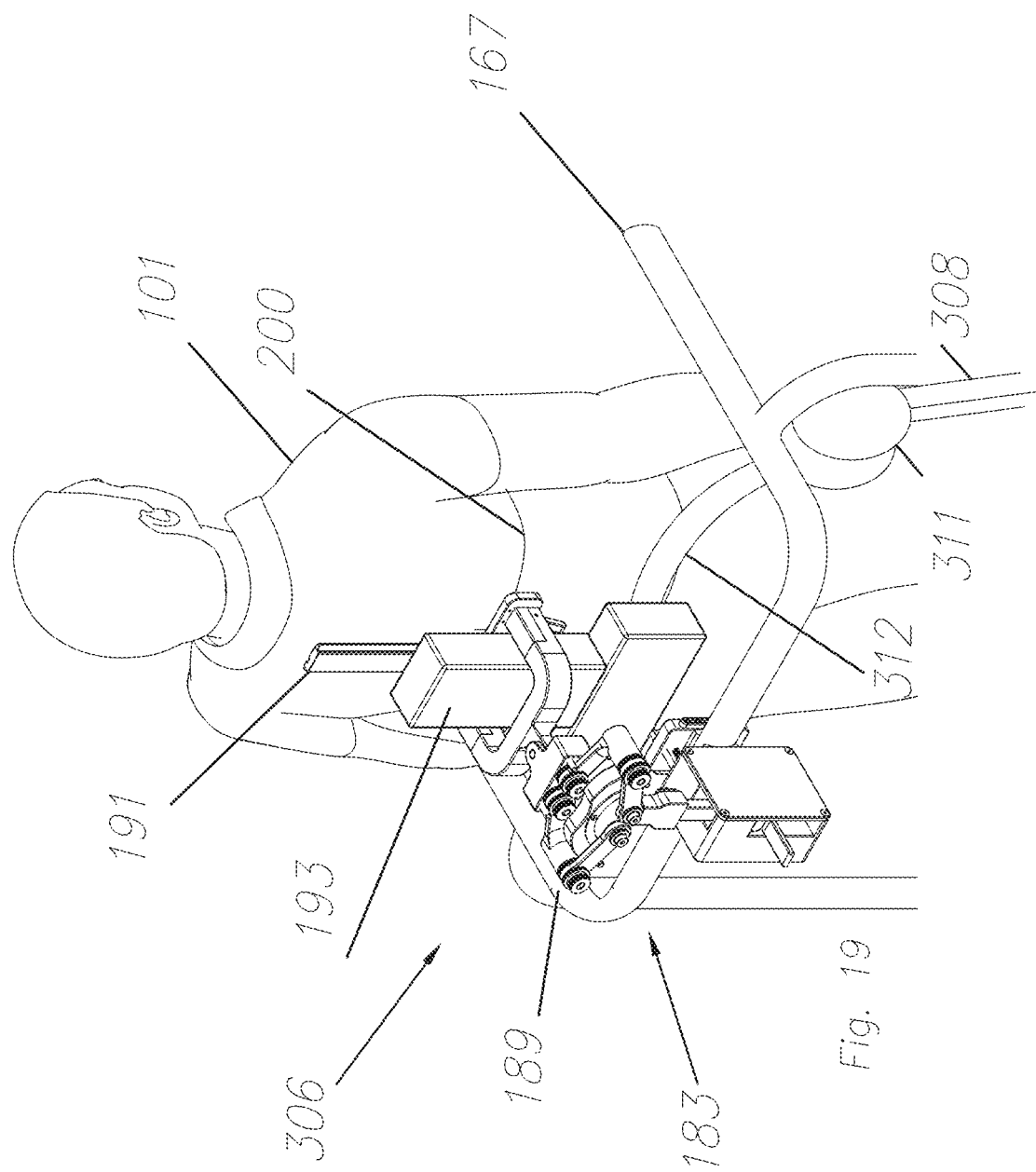

EXOSKELETON SUPPORT MECHANISM FOR A MEDICAL EXOSKELETON

CROSS-REFERENCE TO RELATED APPLICATIONS

This application claims the benefit under 35 U.S.C. § 119(e) of U.S. Provisional Patent Application No. 62/588,824, filed on Nov. 20, 2017, which is incorporated herein by reference in its entirety for all purposes.

STATEMENT REGARDING FEDERALLY SPONSORED RESEARCH OR DEVELOPMENT

This invention was made with government support under Contract No. 1545106 awarded by the National Science Foundation. The government has certain rights in the invention.

TECHNICAL FIELD

The present disclosure pertains to medical exoskeletons. More specifically, described herein are mechanisms that reduce the chance of falling in a medical exoskeleton.

BACKGROUND

Medical exoskeletons are designed to provide locomotion for individuals with mobility disorders. Typically, an exoskeleton is comprised of two leg braces and an upper body brace. Most medical exoskeletons are powered via an assortment of motors, which move the user's body when commanded by the user themselves or a clinician. For most medical exoskeletons, a user supports themselves with the help of two forearm crutches. These crutches are crucial to the user's stability. Without the crutches, the exoskeleton user would fall.

BRIEF DESCRIPTION OF DRAWINGS

FIG. 19 shows another view of an exoskeleton connection feature.

DESCRIPTION OF EMBODIMENTS

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific examples, it will be understood that these examples are not intended to be limiting.

As noted above, medical exoskeletons may implement the use of crutches. According to various embodiments disclosed herein, an "Exoskeleton Support Mechanism" (coupling device) is provided that provides stability for an individual using an exoskeleton. Because of the support provided by the coupling device, medical exoskeleton users now are able to walk without the use of crutches. The coupling devices described below can be used on any medical exoskeleton that typically uses crutches.

Figure 1:
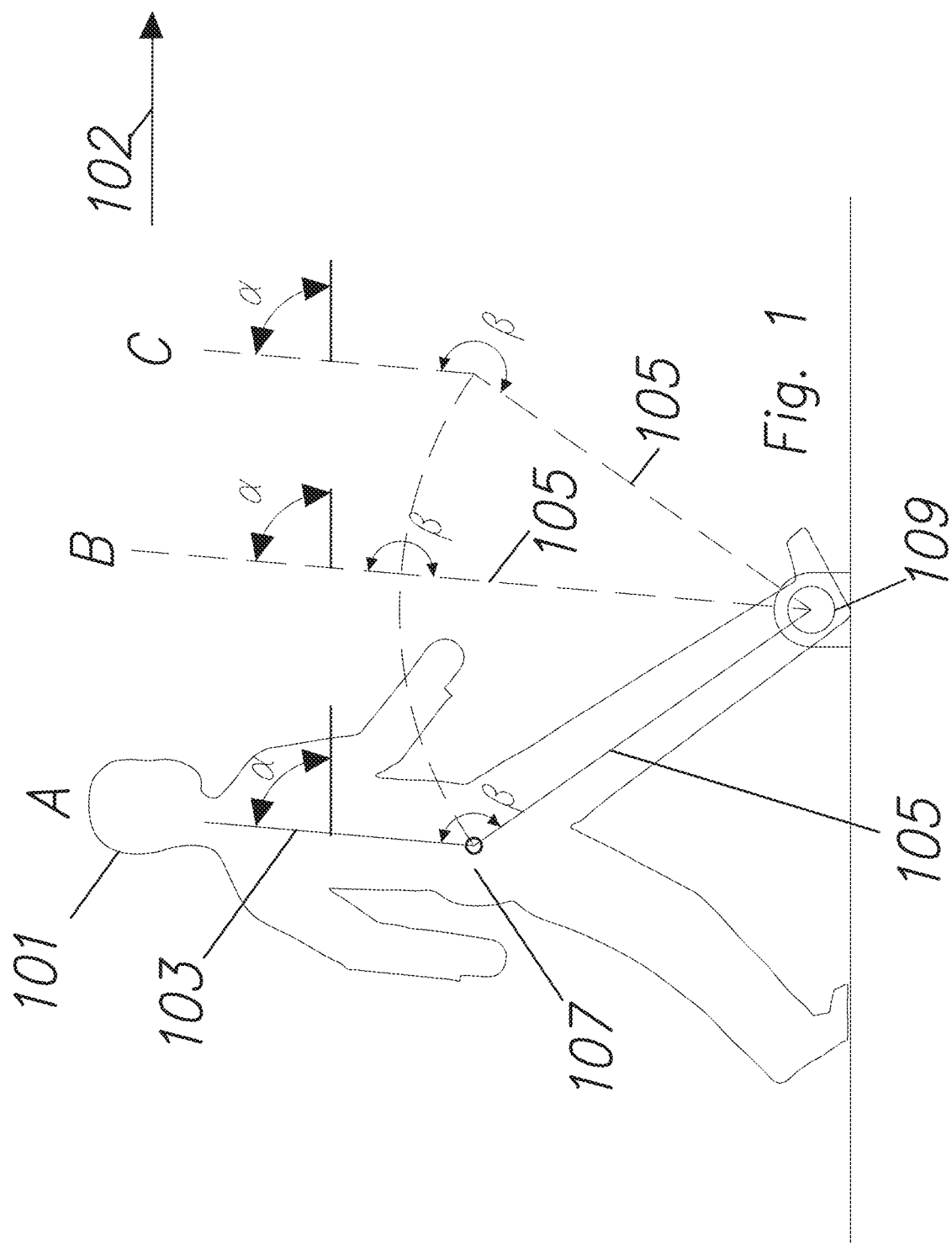
FIG. 1 shows a sagittal view of a person in a double stance.

FIG. 1 shows a sagittal view of a person at a beginning of a single stance of a leg. Accordingly, as person 101 progresses forward, the rear leg of person 101 will lift off the ground (i.e. toe off). After "toe off" has occurred, person 101 will be in single stance and will be supported by leg 105. At this time person 101 is modeled as a simple linkage consisting of person's torso 103 and person leg 105. Person's torso 103 and person's leg 105 are coupled by person hip 107, which is modeled as a rotary joint. Person's leg 105 is on the ground via person ankle 109, which is approximately modeled as a rotary joint. It is assumed that the knee of person's leg 105 maintains complete extension during the stance phase. In some embodiments, a knee joint may be slightly flexed during the stance phase. However, as described in various embodiments, it is assumed that the knee is fully extended. As person 101 contracts specific muscle groups surrounding person's torso 103 and person's leg 105, a torque is produced about person's hip 107. This torque may cause the enlargement of angle $\beta$ as can be seen in FIG. 1. Because the orientation of person's torso 103 remains constant with respect to ground (i.e., torso angle $\alpha$ is constant during locomotion), the torque produced at hip 107 enlarges angle $\beta$ and causes person's torso 103 to proceed along a trajectory from state A through states B and C. If the orientation of person's torso 103 was not constrained to a constant angle (i.e., if angle $\alpha$ was not constant), then when angle $\beta$ increased, person's leg and link 113 would not proceed along a trajectory from state A through states B and C. Furthermore, torso 103 would not proceed along forward direction 102. Accordingly, the orientation of person's torso 103 remaining constant at an angle of $\alpha$ enables the torque generated at person's hip 107 to move person's torso 103 forward and provide locomotion of person 101.

Figure 2:
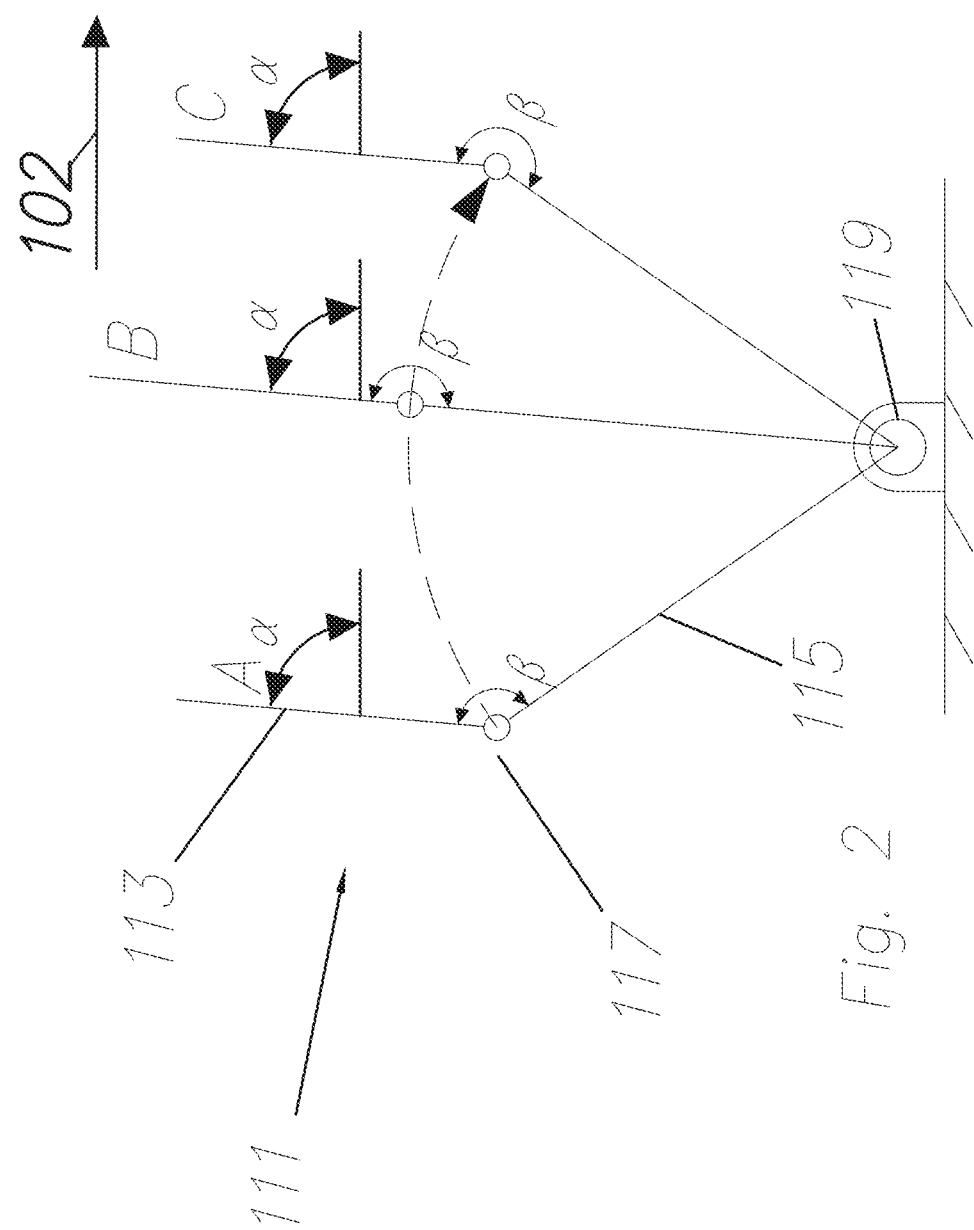
FIG. 2 shows a mechanism representing a leg and torso during a stance.

FIG. 2, shows linkage 111, which models person 101 in FIG. 1. Linkage 111 is a two degree of freedom system. Link 113 represents person's torso 103 and link 115 represents person's leg 105. Joint 117 represents joint of a person's hip 107. If link 113 is constrained such that angle $\alpha$ is held constant, linkage 111 will become a one degree of freedom system and a torque generated at joint 117 will cause link 113 to move forward along forward direction 102.

Figure 3:
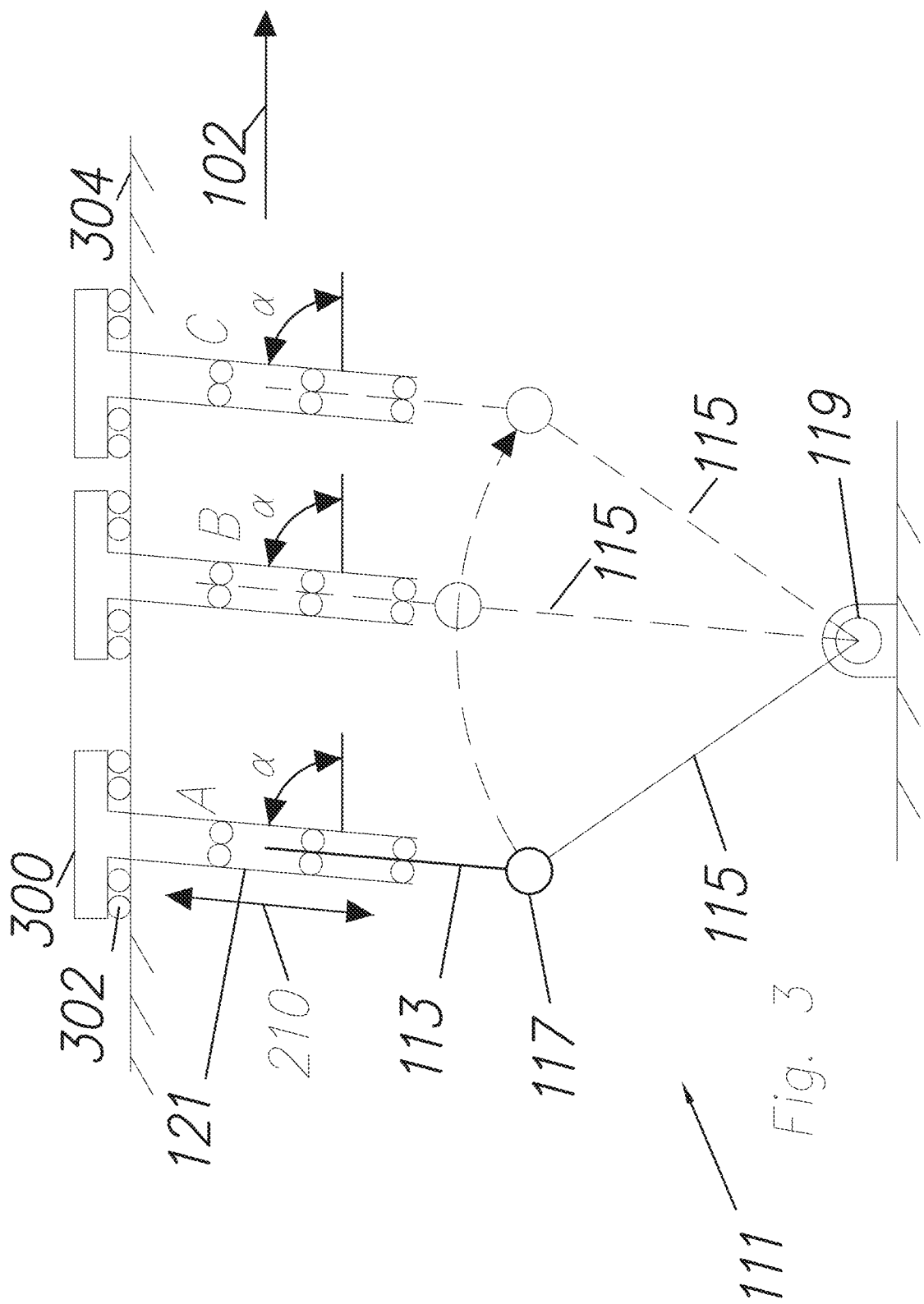
FIG. 3 shows a constrained mechanism representing a leg and torso during a stance.

FIG. 3 shows a mechanism where an additional constraint 121 is applied. Constraint 121 constrains the orientation of link 113 but allows link 113 to move forward along forward direction 102 as well as along free line 210. Trolley 300 is coupled to constraint 121 and can move along forward direction 102. The forward motion of trolley 300 is produced by wheels 302, which are permitted to move along forward direction 102 on surface 304. The addition of constraint 121 reduces the number of degrees of freedom in a mechanism such as linkage 111 from two to one. With constraint 121 applied, any torque produced at joint 117 causes forward motion of link 113 along forward direction 102, while keeping the orientation of link 113 constant. FIG. 3 emulates how locomotion occurs when the orientation of link 113 is constrained. A person with intact mobility constrains the angle of their torso (i.e. angle α) through many muscle activations. However, if a person has a mobility disorder and cannot control their torso angle, said person will not be able to progress forward along forward direction 102.

Figure 4:
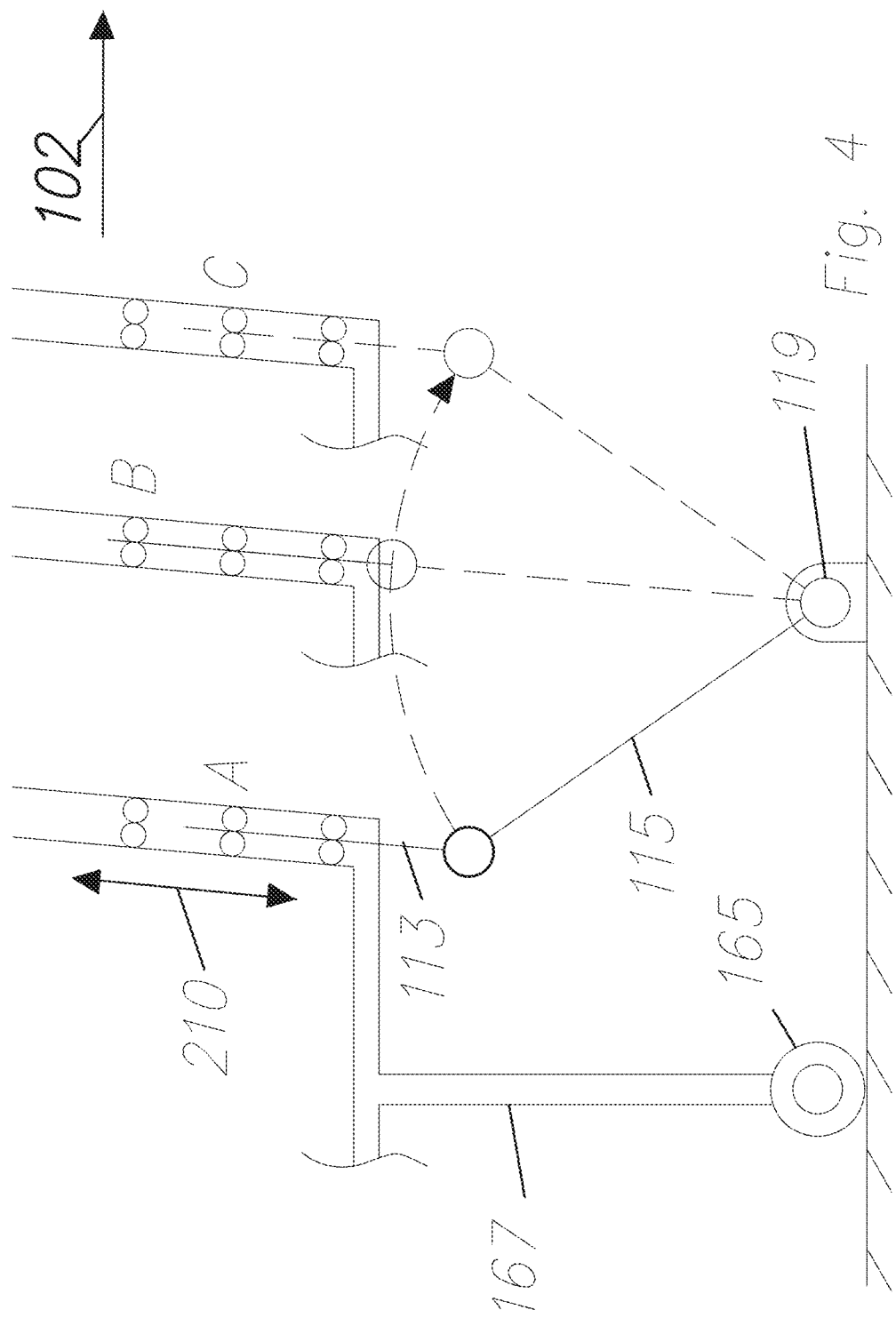
FIG. 4 shows another example of a constrained mechanism representing a leg and torso during a stance.

FIG. 4, as similarly discussed above with reference to FIG. 3, illustrates various embodiments where constraint 121 is made as a part of a walker 167, which is permitted to move on the ground. For illustration purposes, the entire walker is not shown. In FIG. 4, constraint 121 is coupled to walker 167, which is moving on the ground. As discussed above with reference to FIG. 3, constraint 121 may be coupled to trolley 300 and may move along surface 304.

Thus, as discussed above, constraining an orientation of the torso helps facilitate forward locomotion. As shown in FIG. 4, a person with poor balance can be coupled to a walker, which can act to constrain their torso angle. As long as said person can provide a torque at their hip, the person and the walker, taken as a whole, will move forward. The above procedure can also be applied to a person who has no ability to produce a torque at their hip. In this case, an individual uses an exoskeleton to produce said hip torque. The exoskeleton torso is coupled to a walker and also is able to constrain the person's torso angle. In such embodiments, if the exoskeleton can provide a torque at the person's hip, the person and the walker, taken as a whole, will move forward. In the case where the person walks with the assistance of an exoskeleton and walker, the person will remain stable (i.e. will not fall) because the walker has four wheels. Therefore, the person is always stable since the center of mass remains within the footprint of the walker's four wheels. Disclosed herein are coupling devices that couple a person 101 to a walker 167 while constraining the person torso angle.

Figure 5:
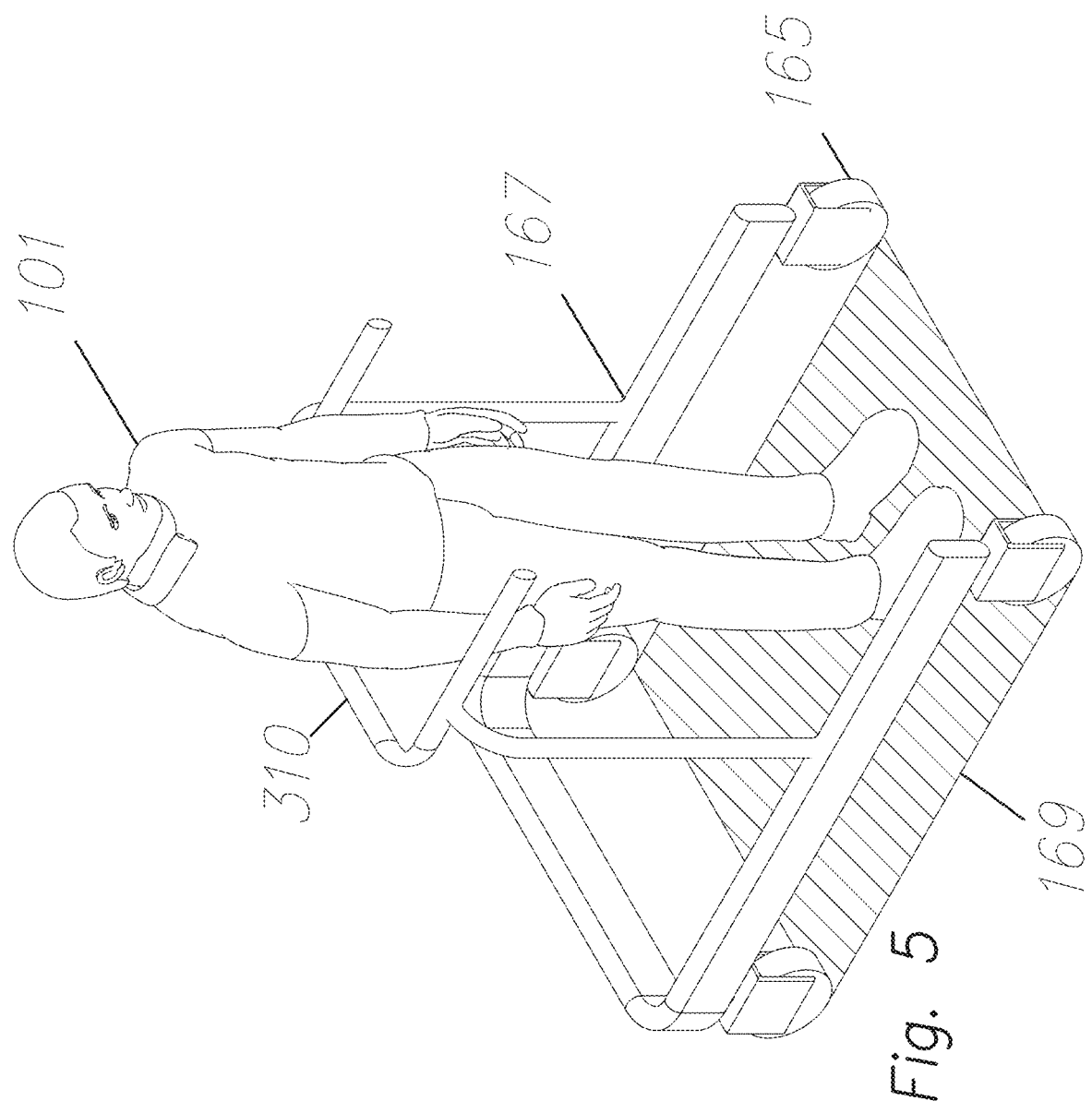
FIG. 5 shows an example of a person standing inside of a walker.

FIG. 5 shows person 101 standing inside of walker 167. As discussed above and discussed in greater detail below, person 101 may be attached to walker 167 in a variety of ways. In some embodiments, walker 167 includes four wheels. In one example, two of the wheels are always behind person 101 and two of which are always in front of person 101.

Figure 6:
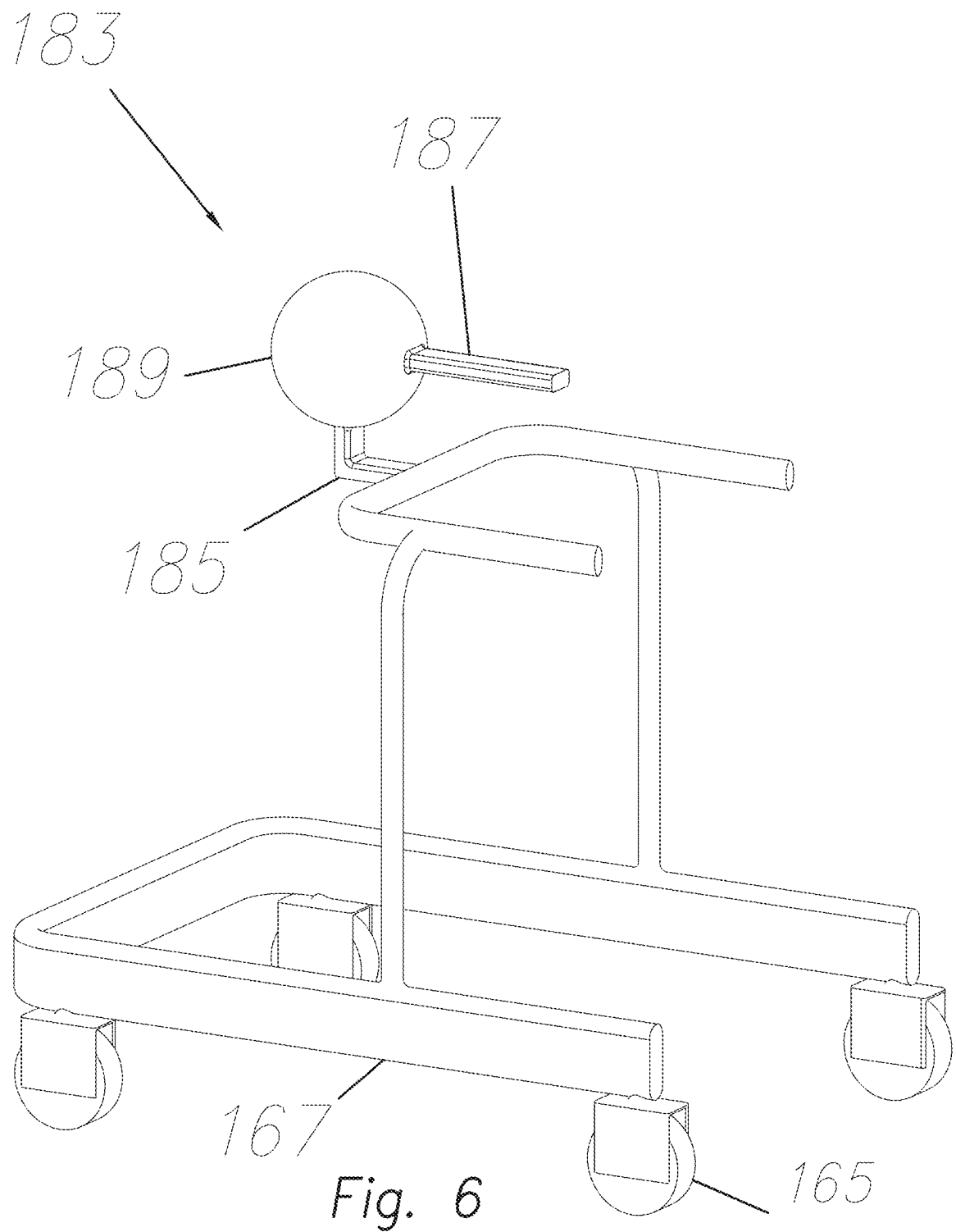
FIG. 6 shows an example of a coupling device.

FIG. 6 shows an example of a coupling device. As will be discussed in greater detail below, a coupling device 183 may include various components such as mechanism 189, orthosis coupling member 187, walker coupling member 185, walker 167, and a wheel, such as wheel 165.

Figure 7:
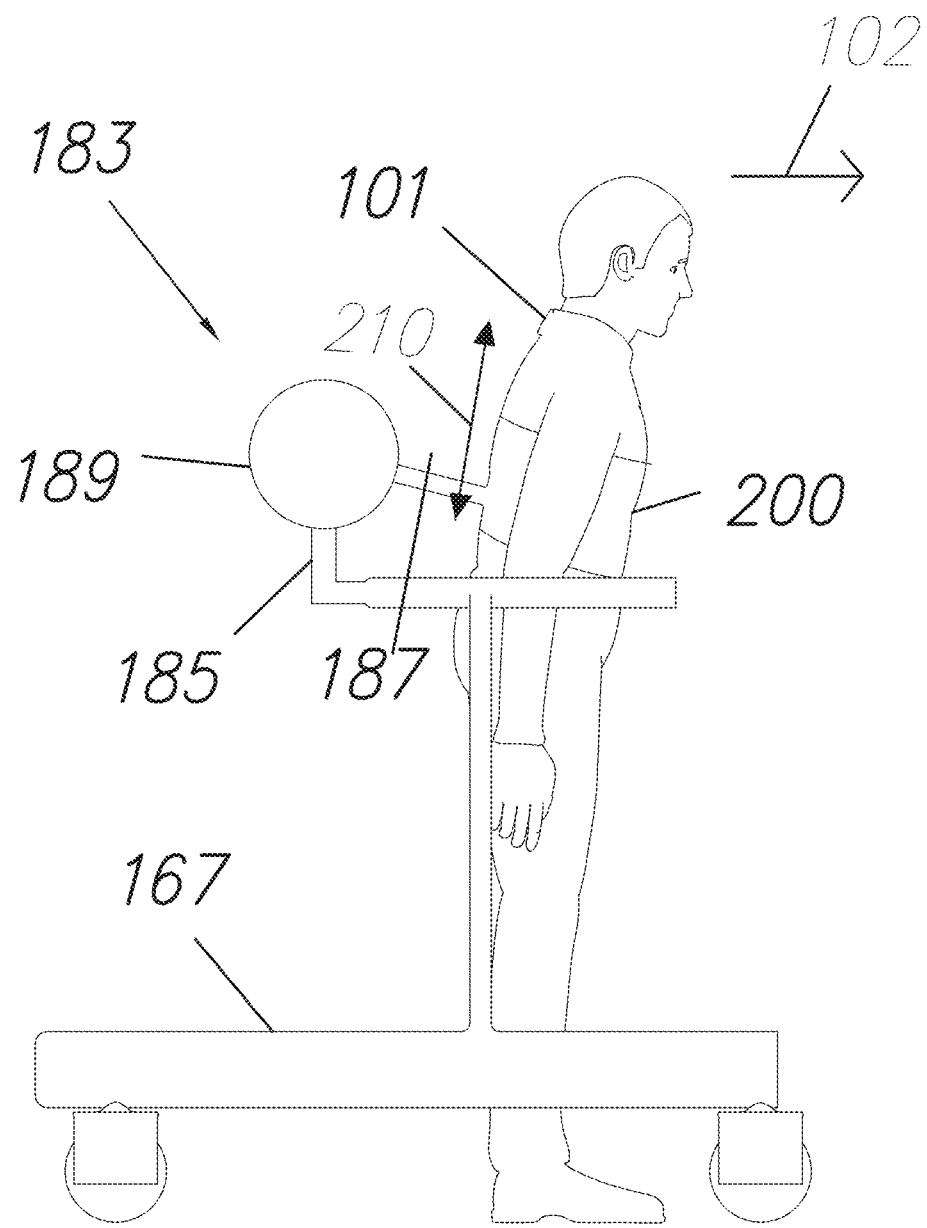
FIG. 7 shows a sagittal view of a person coupled to a walker.

FIG. 7 shows an embodiment of coupling device 183 when it is coupling person 101 to walker 167. Coupling device 183 is configurable to couple walker 167 to torso orthosis 200. Torso orthosis 200 is configurable to couple to person 101. Coupling device 183 comprises an orthosis coupling member 187 which is configurable to be coupled to torso orthosis 200. Coupling device 183 further comprises a walker coupling member 185 which is configurable to be coupled to walker 167. Coupling device 183 further comprises a mechanism 189 which is coupled to orthosis coupling member 187 from its first end and to walker coupling member 185 from its second end. For illustration purposes, FIGS. 6 and 7 do not show all features of mechanism 189, but additional details are provided below. Mechanism 189 is configured such that it constrains orthosis coupling member 187 to move, relative to walker coupling member 185, along a free line 210 (shown in FIG. 4). In some embodiments of invention, free line 210 is a straight line. This freedom to move along free line 210 is needed for locomotion as seen in FIG. 1 where the person's hip 107 moves up and down when traveling through an arc. In operation when torso orthosis 200 is worn by person 101 and coupling mechanism 189 is coupled to both walker 167 and torso orthosis 200, coupling mechanism 189 forces walker and torso orthosis (which is coupled to person 101) to move together along moving direction 102. As shown in embodiment of FIG. 7, free line 210 and moving direction 102 are not parallel. In other words, coupling device 183 does not allow walker 167 and person 101 to move relative to each other along free line 210. This causes walker 167 and person 101 to move together as person 101 progresses to move along direction 102.

Figure 8:
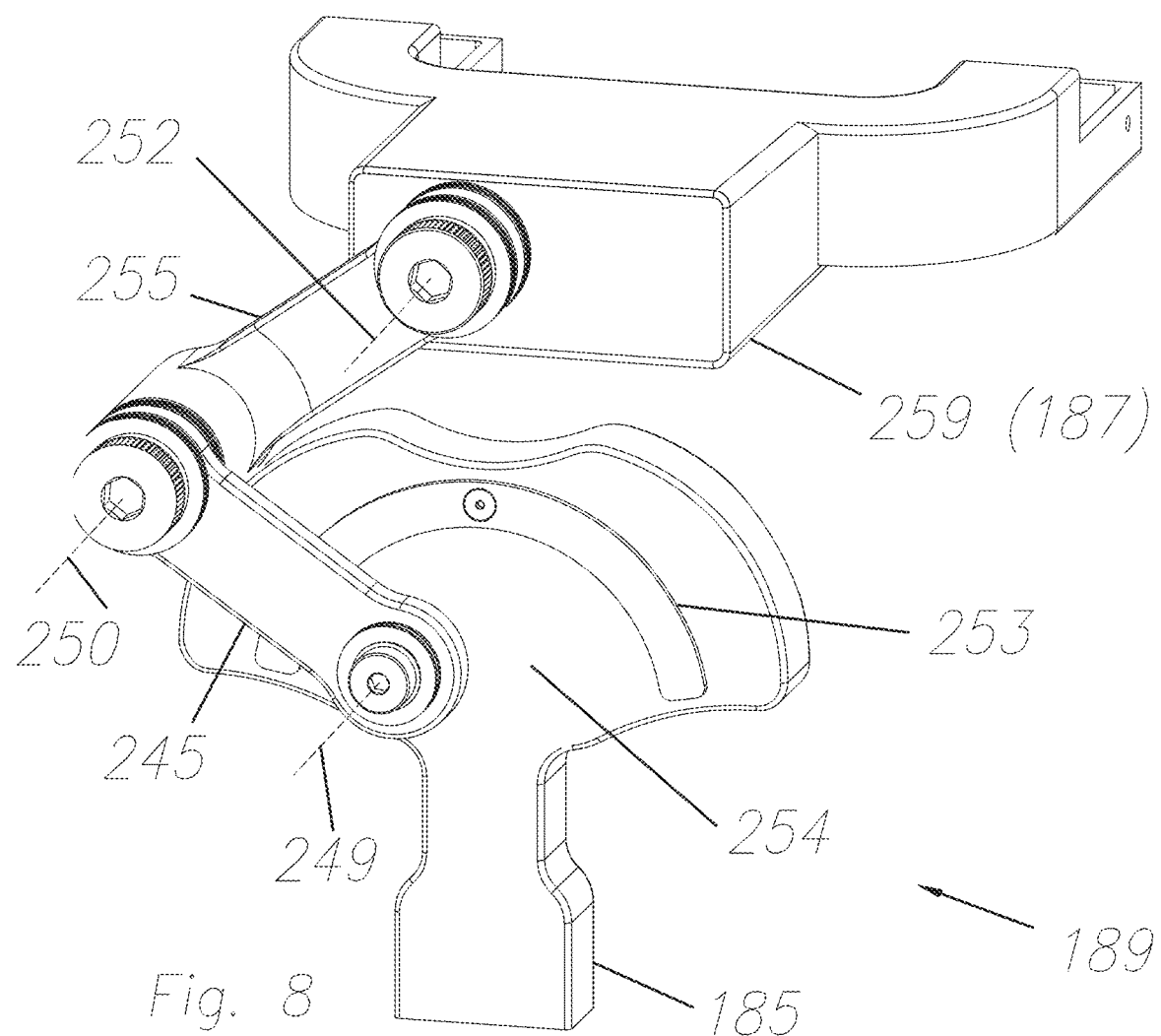
FIG. 8 shows an embodiment of a coupling device.

FIG. 8 shows an embodiment of mechanism 189. In various embodiments, walker coupling member 185 is coupled to walker 167. Such coupling may be implemented by coupling walker coupling member 185 to horizontal bar 310 of walker 167 (as shown in FIG. 6). Link 245 is rotatably coupled to walker coupling member 185 where axis 249 represents the rotation axis. Component 253 may be a low friction material which allows for smooth rotation of link 245. Link 255 is rotatably coupled to link 245 where line 250 represents the rotation axis. Link 259 is rotatably coupled to link 255 where line 252 represents the rotation axis. Together link, 245, 255, and 259 make up a three-bar serial link mechanism which allows link 259 to have three independent degrees of freedom relative to walker coupling member 185. These three independent degrees of freedom exists within a plane parallel to free plane 254.

In various embodiments, mechanism 189 allows for translation and rotation of link 259 in a plane. In some embodiments, link 259 is the same as orthosis coupling member 187 which is coupled to torso orthosis 200. Accordingly, the motion created by this serial link mechanism allows orthosis coupling member 187 to move laterally while coupled to torso orthosis 200. This lateral movement permits weight shifting of person 101 (i.e. the transfer of person 101's body weight off of one leg and onto another leg so as to permit the swinging of an unloaded leg), which occurs when walking in an exoskeleton. As shown by FIG. 8, mechanism 189 allows orthosis coupling member 187 (and by connection link 259) to move and rotate with three degrees of freedom in a plane parallel to free plane 254. This indicates that although torso orthosis 200 is free to move and rotate in this plane, any motion of the orthosis coupling member 187, not in free plane 254, leads to motion of walker coupling member 185.

Figure 9:
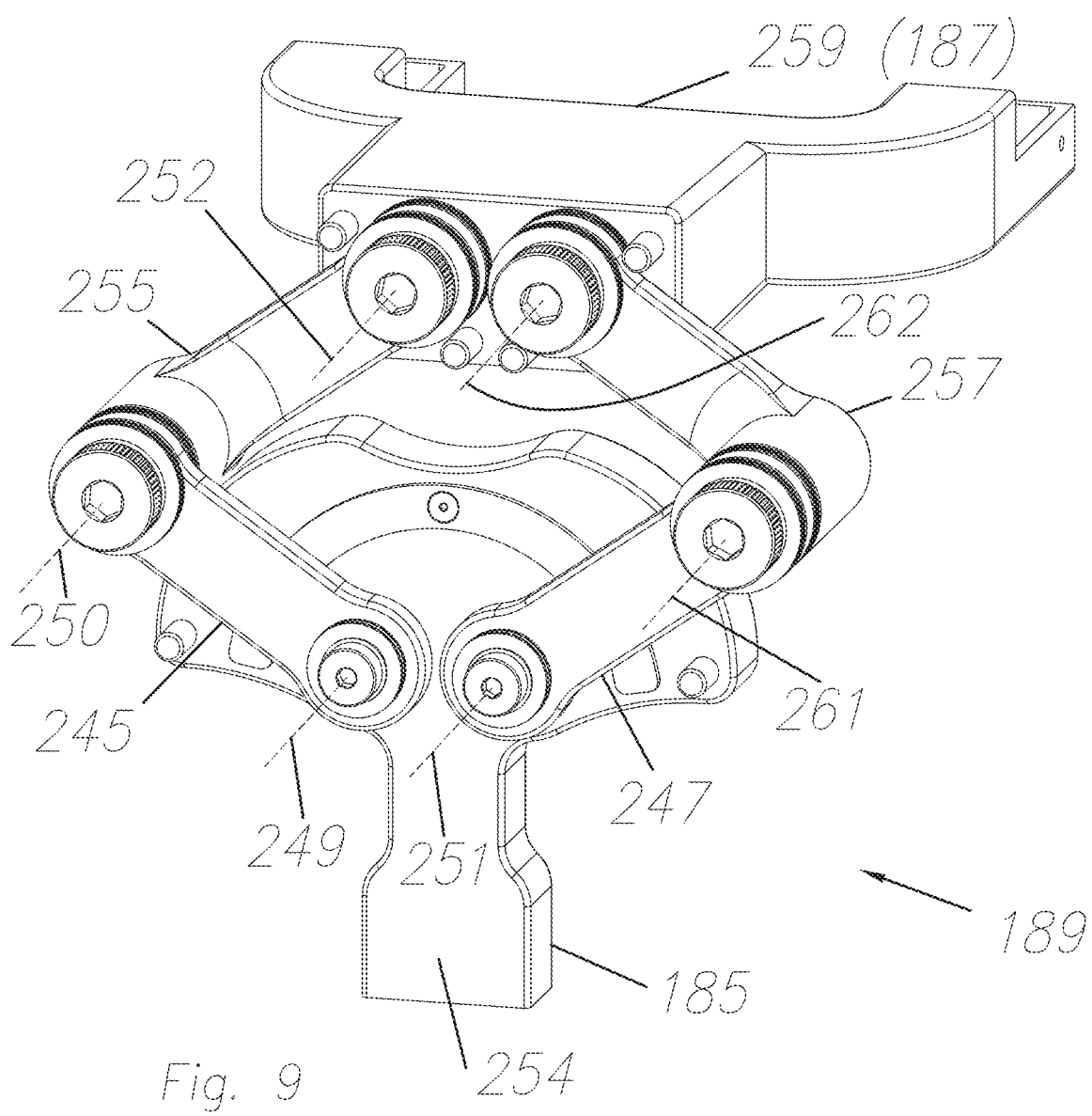
FIG. 9 shows another embodiment of a coupling device.

FIG. 9 shows other embodiments of mechanism 189 that function similarly as the embodiments of FIG. 8, however link 247 and 257 are added, thereby creating a six bar mechanism. Link 247 is rotatably coupled to walker coupling member 185. Axis 251 represents this rotation. Link 257 is rotatably coupled to link 247. Axis 261 represents this rotation. Link 257 is rotatably coupled to link 259. Axis 262 represents this rotation. Like mechanism 189 of FIG. 8, link 259 is able to move and rotate in a plane parallel to free plane 254. However, embodiments of mechanism 189 disclosed by FIG. 9 may be stronger than embodiments of mechanism 189 disclosed by FIG. 8.

Figure 10:
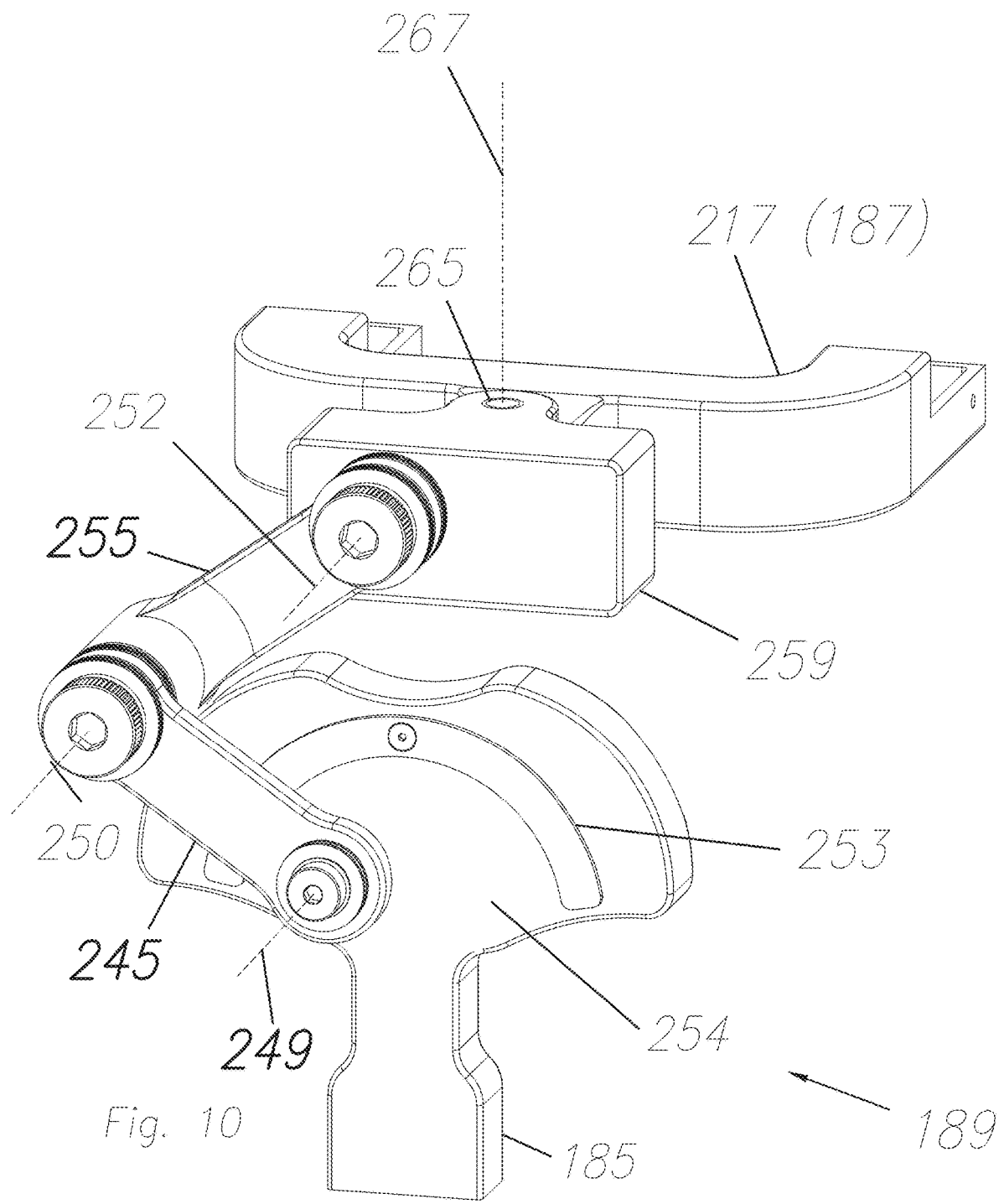
FIG. 10 shows another embodiment of a coupling device.
Figure 11:
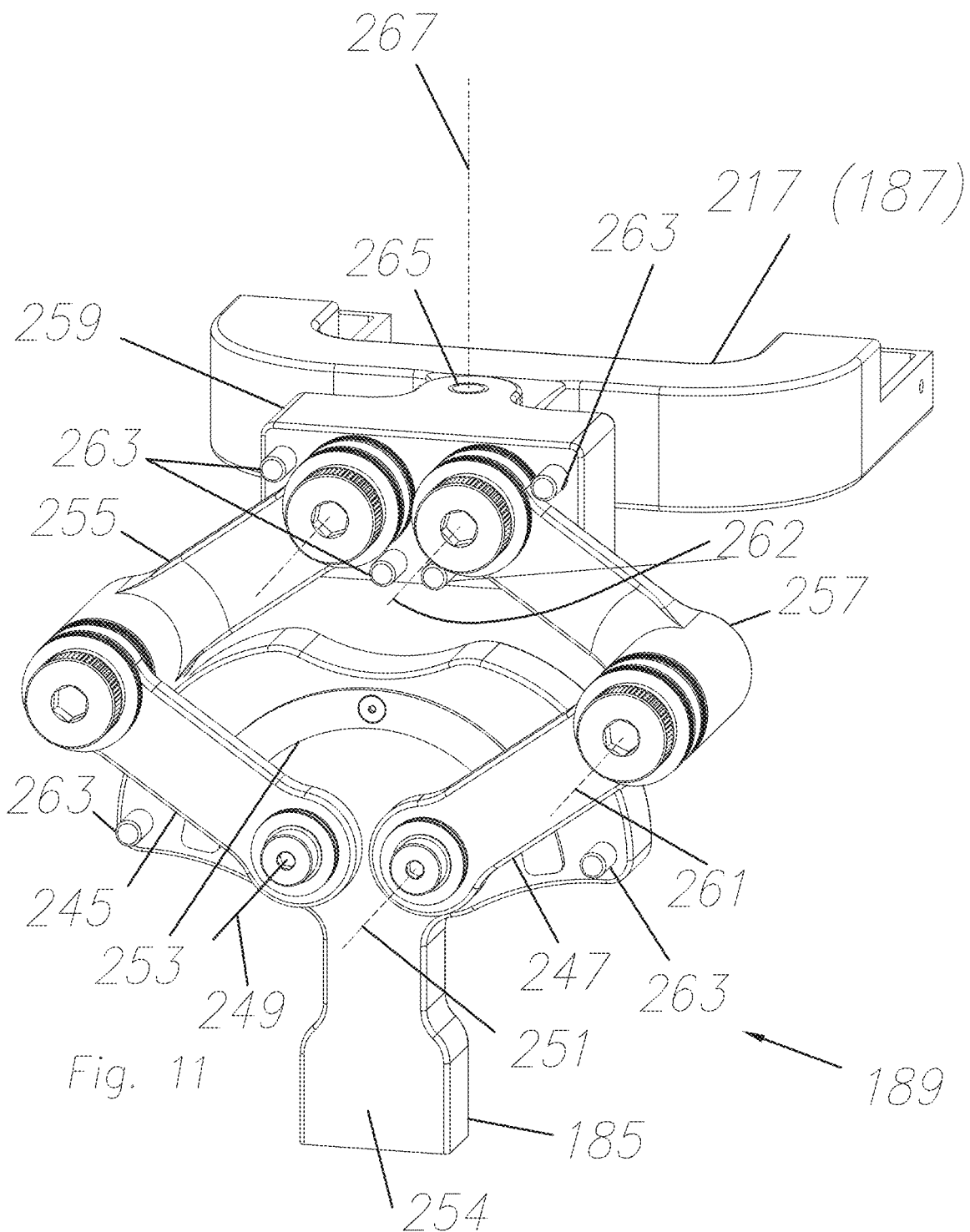
FIG. 11 shows another embodiment of a coupling device.

FIG. 10 shows embodiments where a rotational segment, such as component 217, is rotatably coupled to link 259 at joint 265. Axis 267 shows the axis of rotation of component 217 relative to link 259. In this embodiment, component 217 becomes orthosis coupling member 187 and couples to torso orthosis 200. This rotation of component 217 relative to link 259 constitutes another degree of freedom permitted by mechanism 189. This rotational movement will assist person 101 when attempting to turn walker 167 to walk in a new direction. A similar degree of freedom can be added to the embodiments discussed above with reference to FIG. 9. FIG. 11 shows embodiments where component 217 is rotatably coupled to link 259 at joint 265. Axis 267 shows the axis of rotation. In this embodiment, component 217 is configured as the orthosis coupling member 187.

Figure 12:
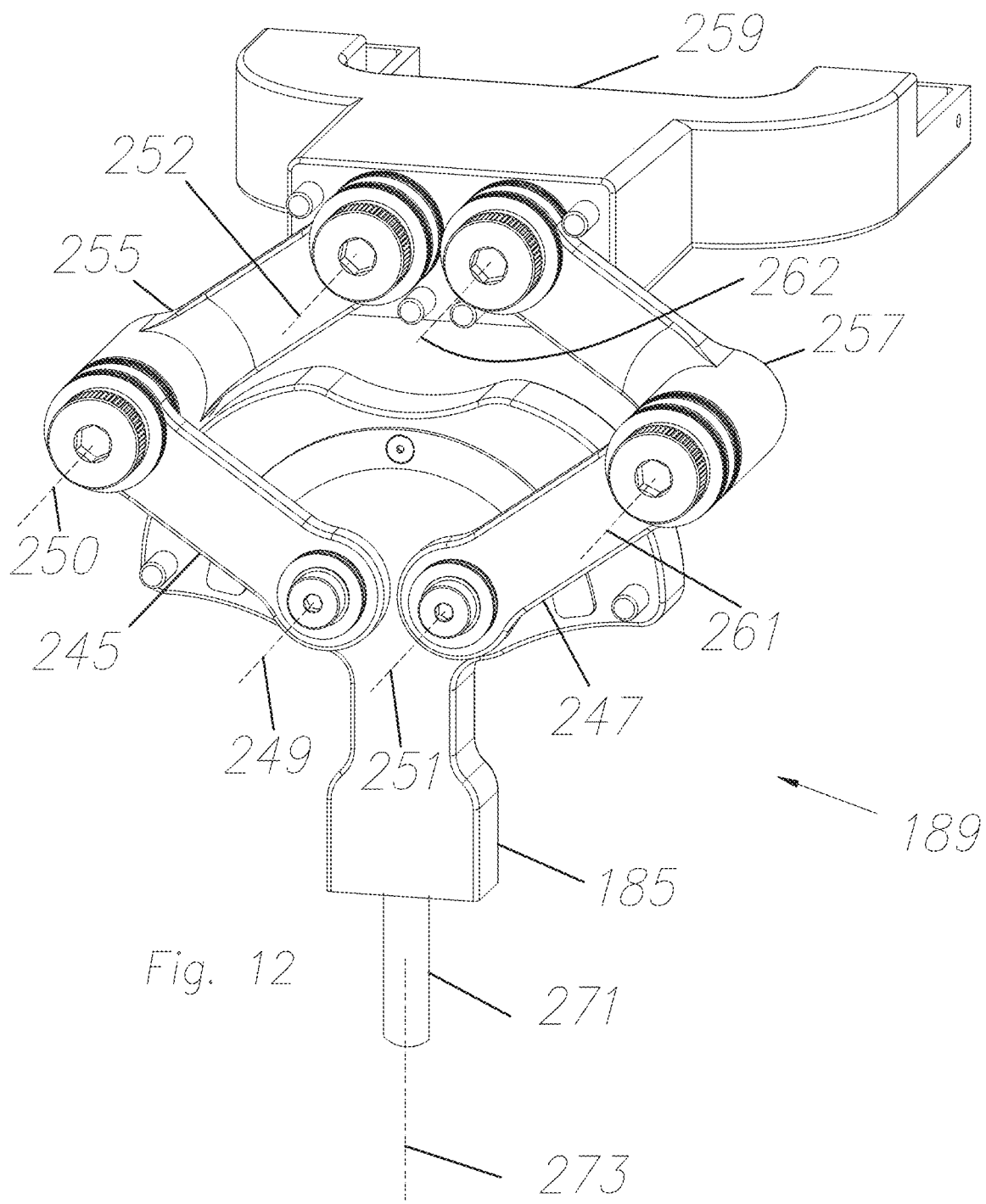
FIG. 12 shows another embodiment of a coupling device.

FIG. 12 an embodiment of mechanism 189 where rotation between link 259 and component 217 is reduced and instead walker coupling member 185 rotates relative to walker 167 about an alternative axis (instead of walker coupling member 185 being fixed relative to walker 167 as shown in FIGS. 10 and 11). In such embodiments, mechanism 189 can rotate relative to walker pin 271 (In this embodiment, walker pin 271 is fixed relative to walker 167) about axis 273. This rotational movement will assist person 101 when attempting to turn walker 167 to walk in a new direction. Accordingly, in some embodiments the order of the rotational degree of freedom and the aforementioned six bar mechanism can be switched. The rotational degree of freedom in FIG. 11 represented by axis 267 is closer to the spine of person 101 than axis 273 of FIG. 12. Accordingly, when person 101 attempts to rotate, person 101 will rotate along a shorter arc length than if person 101 attempts to rotate about axis 273.

Embodiments disclosed herein describe coupling devices 183 that are configurable to couple a walker 167 to a torso orthosis 200. An embodiment of the torso orthosis 200 is described above and shown in FIG. 7. The torso orthosis 200 is configurable to couple to a person 101. Torso orthosis 200 can be a part of an exoskeleton 306 as shown in FIG. 19. As will be discussed in greater detail below, FIG. 19 illustrates embodiments where coupling device 183 is coupled to the back of the torso orthosis 200 which is labeled as exoskeleton spine 191. Accordingly, torso orthosis 200 may be an orthosis that embraces the person's torso area (i.e. upper body or above hip). In various embodiments, such a torso orthosis can be used alone, or it can be a part of an exoskeleton. Torso orthosis 200 may be made of hard and soft materials. In this case the torque at the hip is generated at least partly by actuator 311. Actuator 311 rotatably couples exoskeleton leg 308 to a horizontal member 312 of torso orthosis 200. Battery 193 of exoskeleton 306 is mounted on exoskeleton spine 191.

As discussed above, for example with reference to FIG. 7, a coupling device comprises an orthosis coupling member which is configurable to be coupled to the torso orthosis. This coupling takes place either behind the person, like embodiments shown here, or in front the person. Coupling devices described herein may also comprises a walker coupling member which is configurable to be coupled to a walker. In some embodiments of invention, this coupling can be implemented using any suitable mechanism. In some embodiments of the invention, the coupling can be done via welding or various fasteners. In various embodiments, the coupling is designed to include quick connect and disconnect features. According to some embodiments, a coupling device may also include a mechanism which is coupled to the orthosis coupling member from its first end and to the walker coupling member from its second end. The mechanism may be configured such that it constrains the orthosis coupling member to move (and rotate if allowed), relative to the walker coupling member in a subspace of the mechanism. More specifically, the mechanism, such as mechanism 189, is configured such that it allows limited moving freedom of orthosis coupling member relative to walker coupling member.

In some embodiments of the invention, this subspace is a plane 254 (as shown in FIG. 8) where orthosis coupling member 187 moves and rotates relative to walker coupling member 185 in plane 254. In operation, a torso orthosis is worn by a person and a coupling device is coupled to both the walker and torso orthosis. When configured in this way, a person moves along a moving direction 102, as described above. This causes orthosis coupling member 187 to move along moving direction 102 also. If this moving direction is within the free subspace, then walker coupling member 185 will not move. This may be the case because, in free subspace, orthosis coupling member 187 and walker coupling member 185 can move relative to each other. If moving direction 102 is not within the free subspace, then the coupling device forces the walker and torso orthosis to move along moving direction 102 together. Further, mechanism 189 allows the torso orthosis to move freely in free subspace. This movement permits weight shifting of a person (i.e. the transfer of the person's body weight off of one leg and onto another leg so as to permit the swinging of an unloaded leg), which is an essential part of walking in an exoskeleton.

In some embodiments, the free subspace is a free plane 254. This means mechanism 189 allows orthosis coupling member 187 to move and rotate relative to walker coupling member 185 in a free plane 254. In some embodiments, when subspace is a plane, mechanism 189 comprises a serial three-bar linkage to allow orthosis coupling member 187 to move and rotate relative to walker coupling member 185 in free plane 254. In some embodiments, when subspace is a plane, mechanism 189 comprises a three-degree-of-freedom linkage to allow orthosis coupling member 187 to move and rotate relative to the walker coupling member 185 in plane 254.

In some embodiments, the free subspace is a free plane 254 rotatable along an axis 267 parallel to plane 254, as shown in FIGS. 10 and 11, and mechanism 189 constrains orthosis coupling member 187 member to move and rotate in free plane 254 while the plane is rotatable. In some embodiments, when subspace is a plane rotatable along an axis 267 parallel to the plane, mechanism 189 comprises a serial three-bar linkage to allow the orthosis coupling member to move and rotate relative to the walker coupling member in the free plane. In some embodiments, when subspace is a plane rotatable along an axis parallel to free plane, mechanism 189 comprises a three-degree-of-freedom linkage to allow orthosis coupling member 187 to move and rotate relative to the walker coupling member 185 in plane 254.

Figure 13:
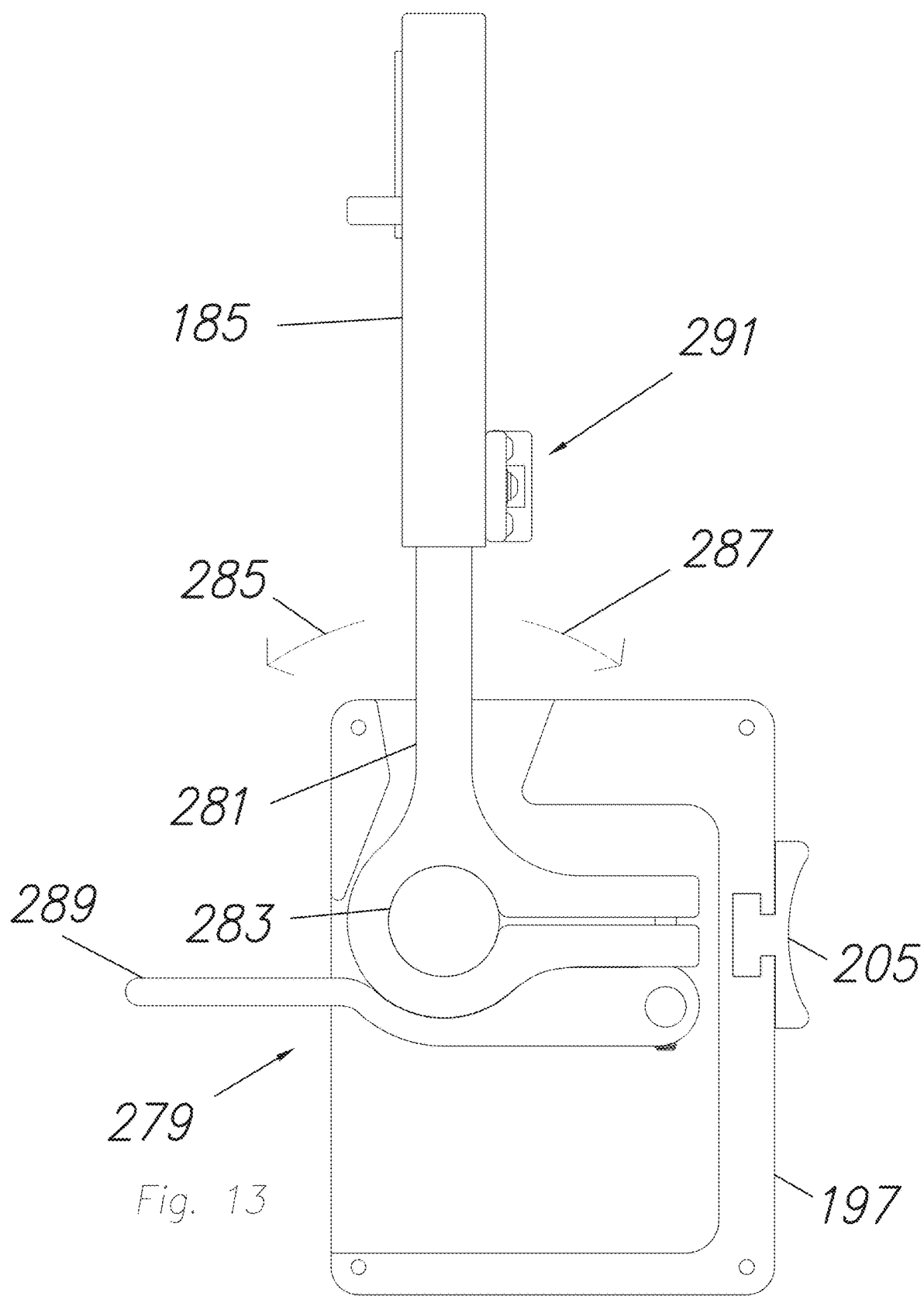
FIG. 13 shows an embodiment of a torso angle adjustment feature and a height adjustment feature of a coupling device.

In some embodiments, as shown in FIG. 13, a coupling device may include a height adjustment feature 291. In the context of a walker, this feature allows a coupling device to be used by individuals with various heights. Accordingly, height adjustment feature 291 allows the entirety of a coupling device to become taller or shorter depending on the height of user such as person 101 and the height of walker 167, described above. In some embodiments of the inventions, a height adjustment feature, such as link 245 described above, is a tool-less feature, allowing for easy adjustment by any user. In some embodiments of invention, height adjustment feature 291 uses fasteners to prevent the translation of walker coupling member 185 relative to holding shaft 281. Via height adjustment feature 291, walker coupling member 185 is able to slide up and down holding shaft 281 and lock in place at discrete steps.

Figure 14:
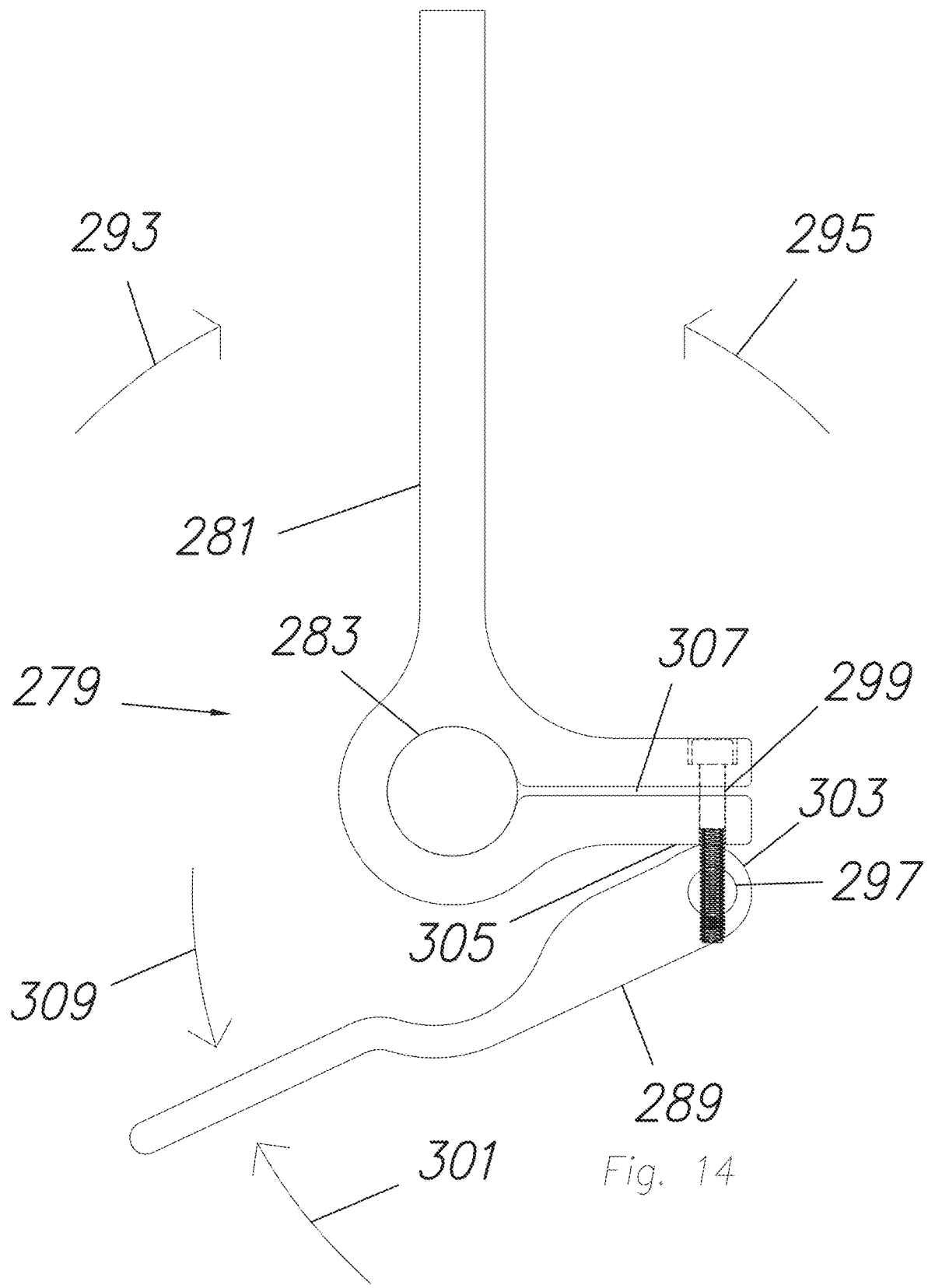
FIG. 14 shows a side profile of a torso angle adjustment feature.
Figure 15:
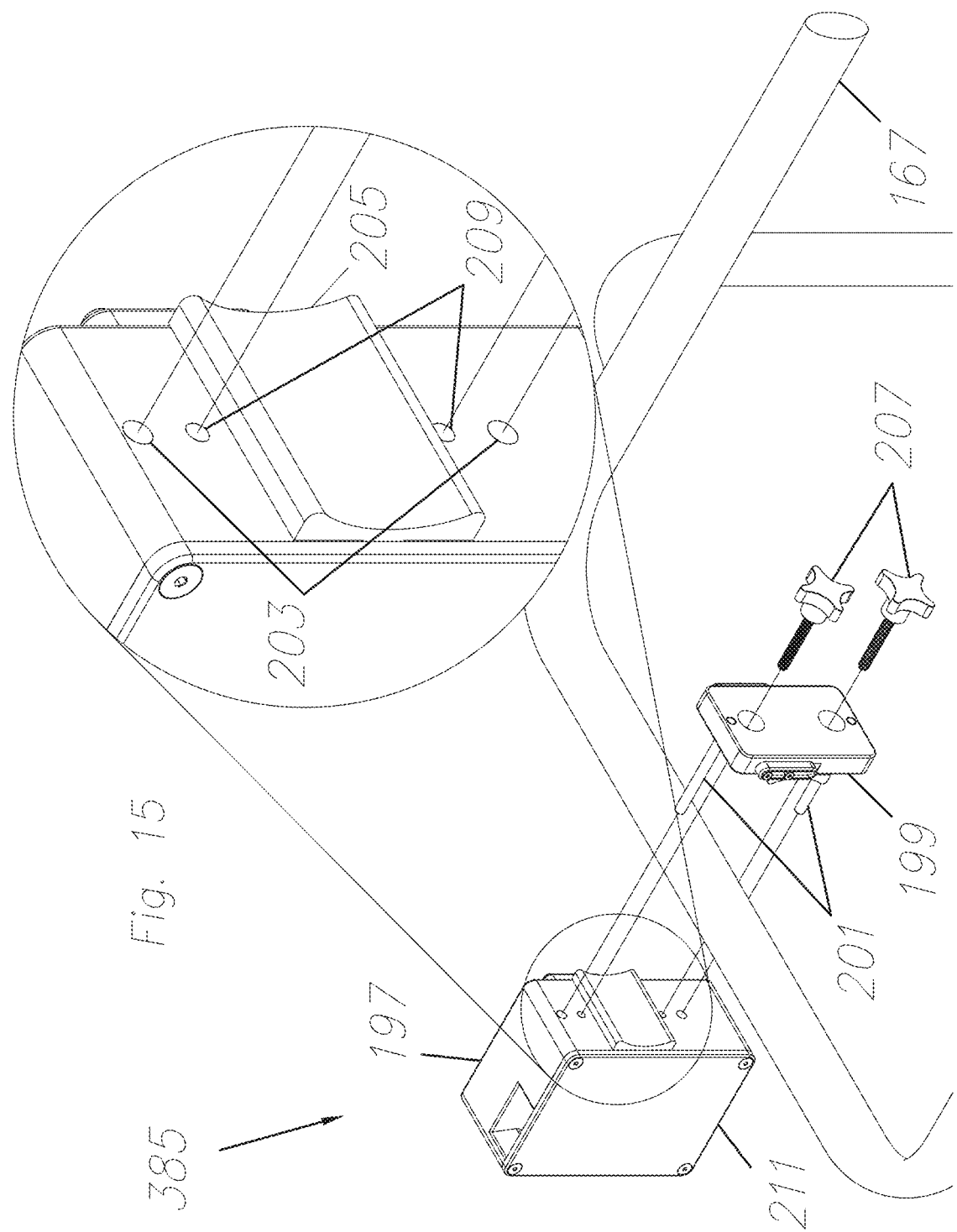
FIG. 15 shows a view of a walker connection feature.

FIG. 15 shows an embodiment of walker connection feature 385. Walker connection feature 385 connects coupling device 183 to walker 167. It will be appreciated that FIG. 15 is a simplified illustration of walker connection feature 385. According to various embodiments, a human such as person 101, the exoskeleton worn by person 101, and the rest of coupling device 183 may be included in FIG. 15. However, for the purposes of clarity of walker connection feature 385, the aforementioned components have not been shown in FIG. 15. In various embodiments, walker connection feature 385 includes container 197 and component 199—each of which may be on opposite sides of walker 167. Component 199 is coupled to pins 201, which are pressed into component 199. By guiding pins 201 into holes 203, component 199 can be moved toward container 197. Additionally, inserts 205 are attached to container 197 and component 199 (insert 205 on component 199 is not labeled in FIG. 14) to ensure solid contact between walker connection feature 385 and walker 167. Inserts 205 are designed with contoured faces identical to that of walker 167's cross section. Once container 197 and component 199 are aligned via pins 201, knobs 207 can be screwed into threaded holes 209 on container 197 and tightened by hand. This tightening allows inserts 205 to clamp firmly around walker 167. In various embodiments, container 197 may also be coupled via fasteners to component 211. In some embodiments, component 211 and container 197 can be treated as the same body.

Figure 16:
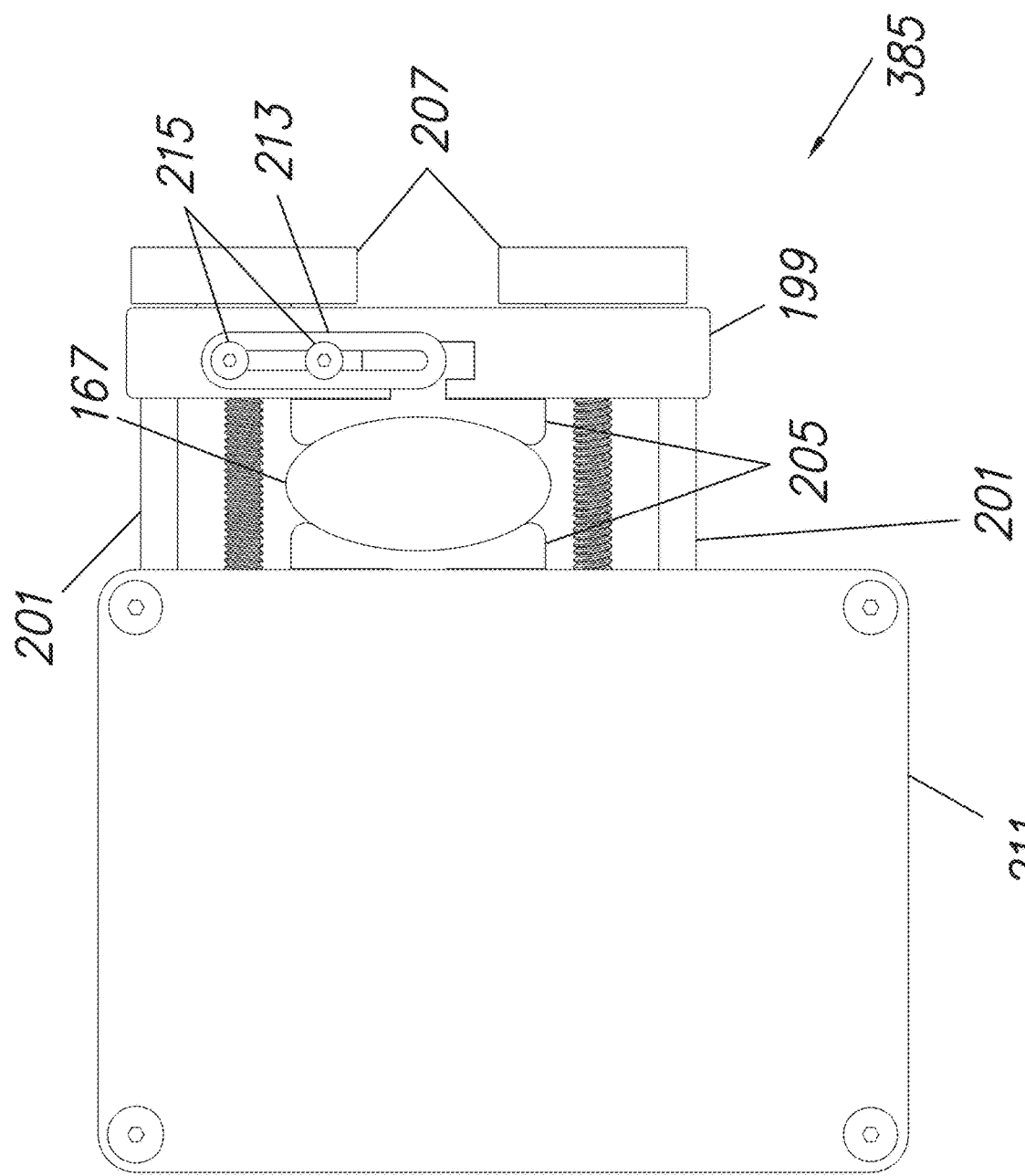
FIG. 16 shows another view of a walker connection feature.

FIG. 16 shows an alternative view of walker connection feature 385. In FIG. 16, component 199 and component 211 are shown. Components 199 and 211 are aligned via pins 201 and are clamped together via the hand tightening of knobs 207. As mentioned earlier, the actual contact between walker connection feature 385 and walker 167 occurs via inserts 205. FIG. 16 provides a cross sectional view of inserts 205 and walker 167. From FIG. 16, it can be seen that the contacting face of inserts 205 are contoured to match the cross sectional shape of walker 167. This match in shape between inserts 205 and the cross section of walker 167 allows for a rigid connection between walker 167 and walker connection feature 385. In various embodiments, coupling device 183 (and in particular, walker connection feature 385) is designed to be compatible with walkers of all shapes and sizes. For example, custom inserts 205 may be designed for each walker 167 that is desired for use. Thus, inserts 205 may be configured to be easily interchangeable in order to attach coupling device quickly from one walker to the next. Accordingly, container 197 and component 199 are configured such that inserts 205 can easily slide in and out of said components.

On both front and back sides of component 199 (the front side is shown in FIG. 16 but the above discussion regarding design applies to the back side of component 199), component 213 is attached to component 199 via fasteners 215. Fasteners 215 are configured to attach component 213 to 199, and fasteners 215 are configured to constrain component 213 to move only up and down relative to component 199. If walker connection feature 385 is in the orientation shown in FIG. 16, and if gravitational acceleration acts downwards, component 213 naturally rests as shown in FIG. 16, thereby preventing insert 205 from sliding out of component 199 unintentionally (which could lead to failure of coupling device 183). In various embodiments, insert 205 can be removed from component 199 manually. In some embodiments, the same constraint technique of insert 205 applies to the back side of container 197 (container 197 can be seen in FIG. 15). However, insert 205 is prevented from sliding out the front side of container 197 via the presence of component 211, which is rigidly attached to container 197 via fasteners. Once knobs 207 are hand tightened, compressive forces bind inserts 205 to container 197 and component 199, essentially making components 213 act as secondary locking features. Components 213 are configured to facilitate swapping of inserts 205 when coupling device 183 is not in use. This design allows coupling device 183 to be easily used amongst any walker regardless of shape. It will be appreciated that walker connection feature 385 requires no use of tools, thereby making this feature easy to use for any individual.

Figure 17:
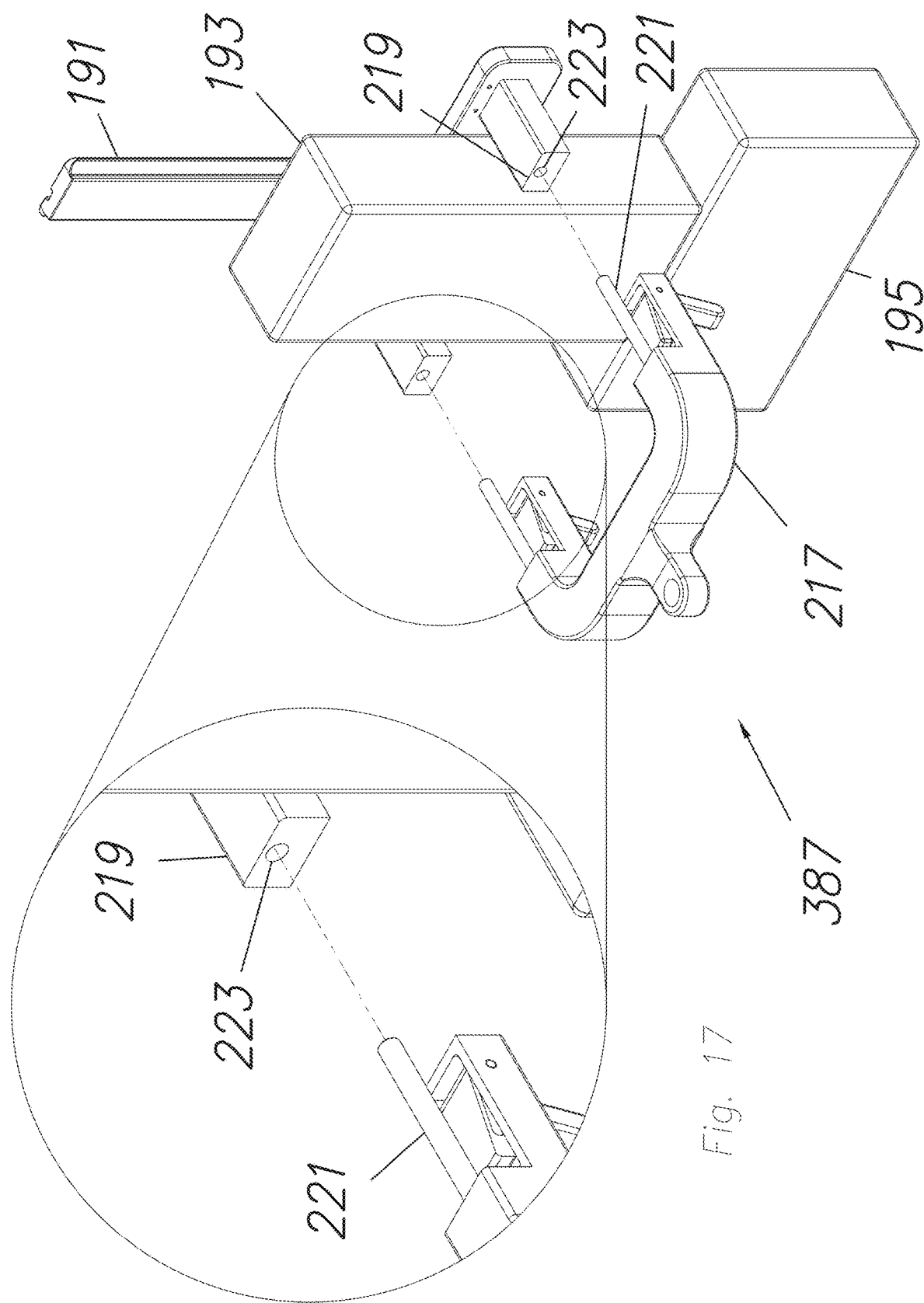
FIG. 17 shows a view of an exoskeleton connection feature.

FIG. 17 provides an embodiment of exoskeleton connection feature 387. Exoskeleton connection feature 387 connects coupling device 183 to the exoskeleton being worn by person 101. As similarly discussed above, FIG. 17 is a simplified illustration of the exoskeleton connection feature 387. More specifically, person 101, walker 167, and the rest of coupling device 183 may be included in FIG. 17, but have been omitted for purposes of clarity. Exoskeleton spine 191, exoskeleton battery 193, and exoskeleton control board 195 are shown in FIG. 16 to further clarify the functionality of exoskeleton connection feature 387. In various embodiments, exoskeleton connection feature 387 includes components 217 and 219. In various embodiments, there are two components 219—both attached to exoskeleton spine 191 and each on opposite sides of exoskeleton battery 193. On each side of component 217 lies pin 221. Pins 221 are pressed into component 217 and face components 219, which both have holes 223 that pins 221 can slide into. This interface between pins 221 and holes 223 comprise the connection of exoskeleton connection feature 387. By guiding component 217 such that pins 221 align with holes 223, an individual can connect the entirety of coupling device 183 to the exoskeleton worn by person 101. To ensure that component 217 cannot separate from components 219 after pins 221 are aligned in holes 223, a snap fit mechanism is incorporated into exoskeleton connection feature 387. In particular, a non-releasing trap snap fit mechanism may be implemented to provide load bearing capabilities and an optimal failure mode. In some embodiments, two non-releasing trap snap fit mechanisms may be implemented, where one is on each side of exoskeleton connection feature 387.

Figure 18:
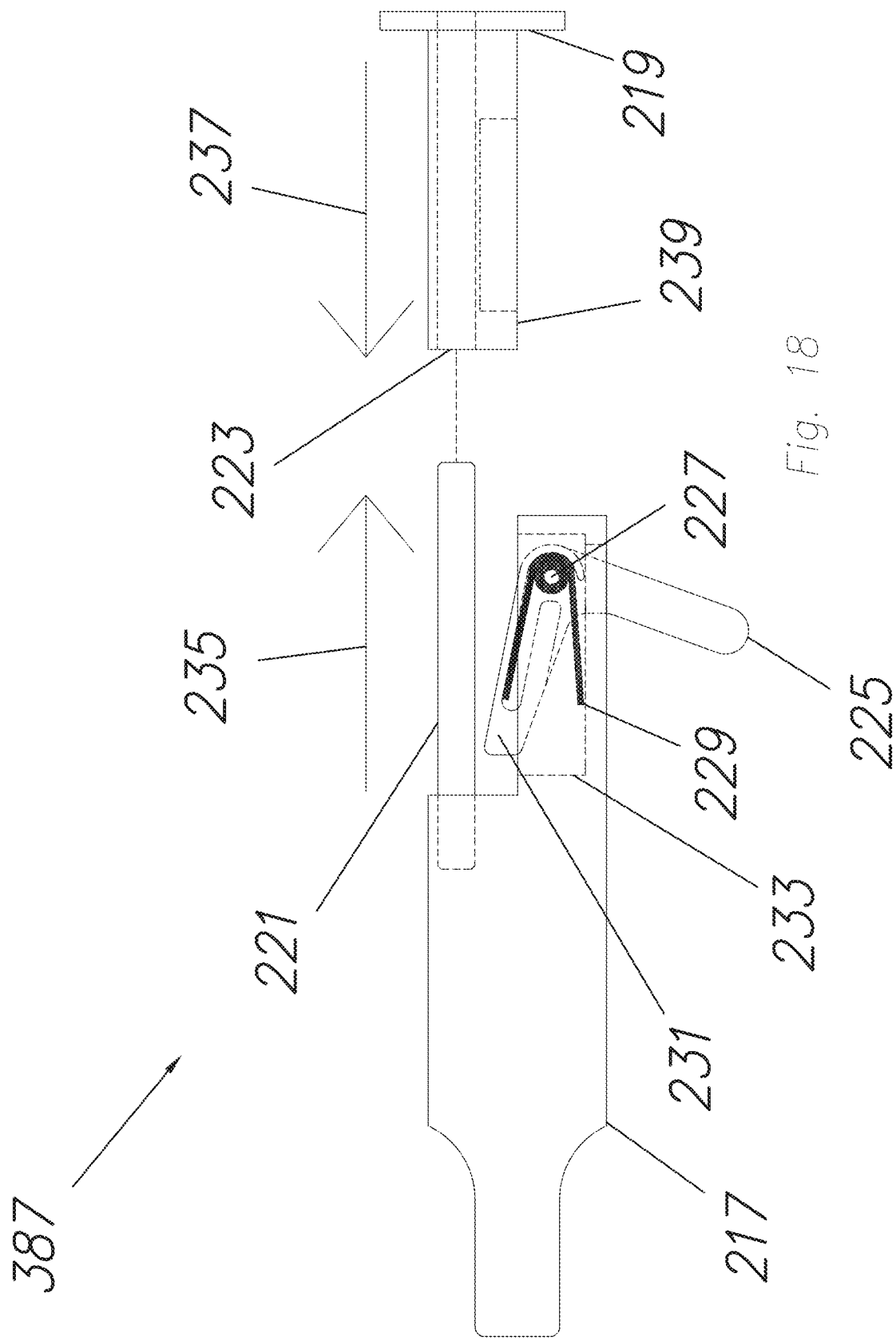
FIG. 18 shows another view of an exoskeleton connection feature.

FIG. 18 shows an embodiment of exoskeleton connection feature 387. As similarly noted above, a particular side is illustrated in FIG. 18, but such features may be implemented on either side of exoskeleton connection feature 387. In FIG. 18, component 217 is shown with pin 221 pressed into component 217. Component 217 is also attached to non-releasing trap 225—which is coupled to component 217 via pin 227. The axis of pin 227 extends into and out of FIG. 18. Thus, non-releasing trap 225 has the ability to rotate relative to component 217 about the axis of pin 227. However, said rotation is controlled via torsional spring 229—which is configured to sit inside non-releasing trap 225 and is concentric to the axis of pin 227. Due to the preload of torsional spring 229, in its assembled state, non-releasing trap 225 sits such that trap section 231 of non-releasing trap 225 rises above cavity 233 in component 217. To couple component 217 with component 219, component 217 is moved along the direction of arrow 235 and component 219 is moved along the direction of arrow 237 until pin 221 aligns with hole 223. In order for the non-releasing trap snap fit mechanism to function, pins 221 contact holes 223 before component 217 contacts components 219. As discussed above, the may be two pins 221 and two holes 223 in exoskeleton connection feature 387. Thus, if both pins 221 and both holes 223 align together, component 217 and components 219 are reduced to a one degree of freedom system. Accordingly, once the alignment of pins 221 and holes 223 occurs, component 217 and components 219 can only slide along the direction of the axes of pins 221. This reduction in degrees of freedom forces face 239 of component 219 to attempt to slide over trap section 231 as components 217 and 219 are brought together. As a result, non-releasing trap 225 is forced to rotate about the axis of pin 227 such that trap section 231 is lowered into cavity 233.

FIG. 19 shows an embodiment of exoskeleton connection feature 387 when components 217 and 219 have been fully connected. As discussed above in FIG. 18, face 239 of component 219 slides over trap section 231, non-releasing trap 225 rotates about the axis of pin 227 such that trap section 231 is lowered into cavity 233. Once face 239 has completely passed over trap section 231, non-releasing trap 225 now sits under cavity 241 of component 219. Due to the open space created by cavity 241 and the preload of torsional spring 229, non-releasing trap 225 rotates back to its original position as seen in FIG. 17. Once this happens, components 217 and 219 are locked together. Attempting to separate the two results in trap section 231 contacting a wall of cavity 241, thereby preventing linear motion between components 217 and 219. Thus, the embodiment of FIG. 19 represents the configuration where coupling device 183 has successfully been attached to the exoskeleton of person 101.

In order to release coupling device 183 from the exoskeleton of person 101, non-releasing trap 225 may be rotated about pin 227 such that trap section 231 is lowered back into cavity 233. This motion will allow components 217 and 219 to slide away from each other until pins 221 are fully removed from holes 223. Trap section 231 may be lowered back into cavity 233 if the lower portion of non-releasing trap 225 (i.e. the only part of non-releasing trap 225 that is exposed in FIG. 18) is manually manipulated such that a counter-clockwise torque is provided on non-releasing trap 225 about the axis of pin 227. Without this manual input from a user, exoskeleton connection feature 387 will not separate. Furthermore, the non-releasing snap-fit mechanism implemented in exoskeleton connection feature 387 may provide additional benefits. First, the connection and disconnection of components 217 and 219 require no tools, thereby making the connection process possible for any user. Second, is that the trap snap fit mechanisms in general are optimal for load bearing applications.

It will be appreciated that person 101 (who is of considerable weight) is ultimately attached to components 219. Additionally, it will be appreciated that coupling device 183 is ultimately attached to component 217 and is responsible for supporting person 101. In order to provide this support, exoskeleton connection feature 387 is configured to support the weight of person 101. As shown in FIG. 18, under a load-bearing scenario, components 217 and 219 will experience forces that attempt to draw them apart from each other, thereby placing significant load on trap section 231 of non-releasing trap 225. However, this load is compressive in nature, making buckling the primary failure mode for non-releasing trap 225. Buckling may be a preferred failure mode for load bearing applications due to its compressive nature (compared to tension-based failure modes such as beam bending. Thus, the non-releasing snap fit mechanism provides beneficial failure tolerance for exoskeleton connection feature 387.

Although the foregoing concepts have been described in some detail for purposes of clarity of understanding, it will be apparent that certain changes and modifications may be practiced within the scope of the appended claims. It should be noted that there are many alternative ways of implementing the processes, systems, and devices. Accordingly, the present examples are to be considered as illustrative and not restrictive.

What is claimed is:

1. A coupling device, configurable to couple a walker to a torso orthosis, which is configurable to couple to an upper body of a person, said coupling device comprising:
    an orthosis coupling member, configurable to be coupled to said torso orthosis;
    a walker coupling member, configurable to be coupled to said walker; and
    a mechanism, comprising a first end and a second end and coupled to the orthosis coupling member from the first end and to the walker coupling member from the second end,
        wherein said mechanism is configured to constrain said orthosis coupling member to move and rotate relative to the walker coupling member in a free plane and to allow said torso orthosis and said upper body of the person to move and rotate laterally, and
        wherein when said torso orthosis is worn by the person and said coupling mechanism is coupled to both said walker and said torso orthosis, and when said person is walking in a forward direction, said mechanism forces said walker coupling member and said orthosis coupling member to move along said forward direction together, and allows said orthosis coupling member to move and rotate laterally in said free plane for weight shifting during walking.

2. The coupling device of claim 1, wherein said mechanism comprises a serial three-bar linkage configured to constrain said orthosis coupling member to move and rotate relative to said walker coupling member in a said free plane.

3. The coupling device of claim 1, wherein said mechanism comprises a three-degree-of-freedom linkage configured to constrain said orthosis coupling member to move and rotate relative to said walker coupling member in said free plane.

4. A coupling device, configurable to couple a walker to a torso orthosis, which is configurable to couple to an upper body of a person, said coupling device comprising:
    an orthosis coupling member, configurable to be coupled to said torso orthosis;
    a walker coupling member, configurable to be coupled to said walker; and
    a mechanism, comprising a first end and second end and coupled to the orthosis coupling member from the first end and to the walker coupling member from the second end,
        wherein said mechanism is configured to constrain said orthosis coupling member to move and rotate relative to walker coupling member in a free subspace, and
        wherein when said torso orthosis is worn by the person and said coupling mechanism is coupled to both said walker and said torso orthosis, and when said person is walking in a forward direction, said mechanism forces said walker coupling member and said orthosis coupling member to move along said forward direction together and allows said orthosis coupling member to move and rotate laterally relative to the walker coupling member in said free subspace.

5. The device of claim 4, wherein said free subspace comprises a free plane, parallel to a frontal plane of said person, and said mechanism is configured to constrain said orthosis coupling member to move and rotate relative to walker coupling member in said free plane.

6. The coupling device of claim 5, wherein said mechanism comprises a serial three-bar linkage configured to constrain said orthosis coupling member to move and rotate relative to said walker coupling member in said free plane.

7. The coupling device of claim 5, wherein said mechanism comprises a three-degree-of-freedom linkage configured to constrain said orthosis coupling member to move and rotate relative to said walker coupling member in said free plane.

8. The device of claim 4, wherein said free subspace comprises a free plane, parallel to a frontal plane of said person and configured to rotate along an axis parallel to said free plane, and wherein said mechanism is configured to constrain said orthosis coupling member to move and rotate in said free plane relative to walker coupling member.

9. The coupling device of claim 8, wherein said mechanism comprises a serial three-bar linkage configured to constrain said orthosis coupling member to move and rotate relative to said walker coupling member in said free plane.

10. The coupling device of claim 8, wherein said mechanism comprises a three-degree-of-freedom linkage configured to constrain said orthosis coupling member to move and rotate relative to said walker coupling member in said free plane.

11. The device of claim 8, wherein said free subspace is a free line and said mechanism is configured to constrain said orthosis coupling member to move relative to the walker coupling member along said free line.

12. The device of claim 4,
wherein said free subspace comprises a free line, parallel to a frontal plane of said person, and said mechanism is configured to constrain said orthosis coupling member to at least move relative to the walker coupling member along said free line, and
wherein, when said person is walking in a forward direction, said mechanism forces said walker coupling member and said orthosis coupling member to move along said forward direction together and allows said orthosis coupling member to at least move relative to said walker coupling member needed for weight shifting during walking.

13. The device of claim 4,
wherein said free subspace comprises a rotational motion in a frontal plane of said person and said mechanism is configured to constrain said orthosis coupling member to at least rotate relative to walker coupling member in the frontal plane, and
wherein, when said person is walking in a forward direction, said mechanism forces said walker coupling member and said orthosis coupling member to move along said forward direction together and allows said orthosis coupling member to at least rotate relative to said walker coupling member needed for weight shifting during walking.

14. The coupling device of claim 13, wherein said mechanism comprises at least a joint configured to constrain said orthosis coupling member to at least rotate relative to said walker coupling member.

\* \* \* \* \*